United States Patent [19]

Allgeier et al.

[11] 4,076,812
[45] Feb. 28, 1978

[54] 10-HALOGENO- OR 10,11-DIHALOGENO DERIVATIVES OF 5H-DIBENZ[b,f]AZEPINE

[75] Inventors: Hans Allgeier, Haagen, Germany; Erich Schmid, Basel, Switzerland

[73] Assignee: Ciba-Geigy Corporation, Ardsley, N.Y.

[21] Appl. No.: 615,256

[22] Filed: Sep. 22, 1975

[30] Foreign Application Priority Data

Sep. 27, 1974 Switzerland .................. 13095/74

[51] Int. Cl.$^2$ .................. A61K 31/55; C07D 223/22
[52] U.S. Cl. .................. 424/244; 260/239 D
[58] Field of Search .................. 260/239 D; 424/244

[56] References Cited

U.S. PATENT DOCUMENTS 2,762,796  9/1956  Morel et al. .................. 260/239 D

FOREIGN PATENT DOCUMENTS 82,719   6/1971   Germany .................. 260/239 D
914,717  1/1963   United Kingdom .......... 260/239 D
943,277  12/1973  United Kingdom .......... 260/239 D Primary Examiner—Donald G. Daus
Assistant Examiner—D. B. Springer
Attorney, Agent, or Firm—John J. Maitner

[57] ABSTRACT

The present invention relates to new derivatives of 5H-dibenz[b,f]azepine having the formula I

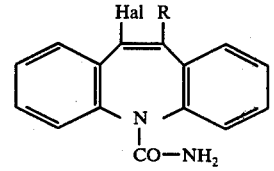

wherein Hal represents halogen with an atomic number up to 35 and R represents hydrogen or halogen with an atomic number up to 35. These new compounds possess useful pharmacological properties, in particular a prolonged anticonvulsive action, and can be used for the treatment of states of convulsion, especially of epilepsy. A specific embodiment of the invention is 10-chloro-5H-dibenz[b,f]azepine-5-carboxamide.

15 Claims, No Drawings

10-HALOGENO- OR 10,11-DIHALOGENO DERIVATIVES OF 5H-DIBENZ[b,f]AZEPINE

DETAILED DESCRIPTION

The present invention relates to new derivatives of 5H-dibenz[b,f]azepine, pharmaceutical compositions which contain these new substances, and the therapeutic use of these new substances.

The derivatives according to the invention of 5H-dibenz[b,f]azepine have the formula I

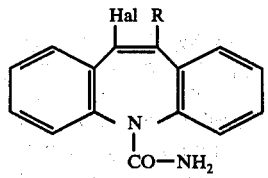

wherein Hal represents halogen with an atomic number up to 35 and R represents hydrogen or halogen with an atomic number up to 35. "Hal" representing halogen is fluorine, chlorine or bromine. Where R is a halogen atom it can have the meaning of "Hal" or be different therefrom; but compounds in which R is hydrogen are particularly preferred.

The compounds of formula I possess useful pharmacological properties, in particular a prolonged anticonvulsive action, as can be determined, for example, in the electric shock test on mice on oral administration of doses between 6 and 35 mm/kg. At the same time their toxicity in comparison to the anticonvulsive action is low and the therapeutic index consequently high. The compounds of general formula I can be used for the treatment of states of convulsion, especially of epilepsy, and are administered orally or rectally.

The compounds of formula I are manufactured by
a. reacting a compound of general formula II

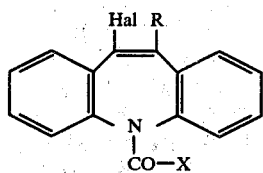

wherein X represents chlorine or bromine, and Hal and R have the meanings assigned to them in formula I, with ammonia, or b. splitting off the hydrogen halide $H-Y_1$ or $H-Y_2$ from a compound of general formula III

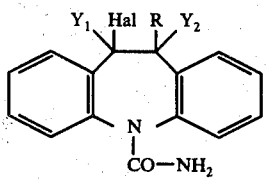

wherein one of the symbols $Y_1$ and $Y_2$ represents hydrogen and the other represents a halogen atom whose atomic numbers is the same as or higher than that of the halogen atom Hal and of the possible halogen atom R.

The reaction in accordance with (a) is preferably carried out in an organic solvent, for example in a lower alkanol, e.g. ethanol, isopropanol or butanol, in an ethereal liquid, such as tetrahydrofuran or dioxan, or in a hydrocarbon, e.g. benzene or toluene, at room temperature or preferably at elevated temperature, for example at the boiling temperature of the solvent employed. The ammonia required can be bubbled in as gas at the start at the reaction or during the entire reaction course, or, if a water-miscible solvent is used, it can also be used as concentrated aqueous solution. It is also possible, however, to use liquid ammonia and to carry out the reaction, if necessary, in a closed vessel.

Starting materials of general formula II are obtained, for example, by reacting the corresponding 10-halogeno- or 10,11-dihalogeno-5H-dibenz[b,f]azepines of general formula IV

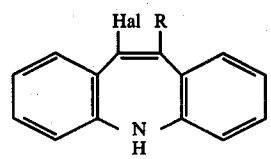

wherein Hal and R have the meanings assigned to them in formula I, with phosgene or carbonic dibromide in an inert organic solvent, for example benzene or especially toluene, at room temperature or moderately elevated temperature. The manufacture of the 10-halogeno- and 10,11-dihalogeno-5H-dibenz[b,f]azepines of general formula IV required for this reaction depends partly on the nature of the halogen atom Hal. 10-Fluoro-5H-dibenz[b,f]azepine is obtained, for example, by starting from known 5-benzyl-5,11-dihydro-10H-dibenz[b,f]azepin-10-one and reacting it with sulphur tetrafluoride and hydrogen fluoride or with selenium tetrafluoride in an inert organic solvent, for example methylene chloride, at moderately elevated temperature, and splitting off the benzyl radical from the resultant 5-benyl-10-fluoro-5H-dibenz[b,f]azepine by hydrogenolysis, for example at room temperature and normal pressure in methanol and using a palladium on charcoal catalyst. 10-Chloro- and 10-bromo-5H-dibenz[b,f]azepine are obtained by adding first, for example, chlorine and bromine respectively to 5-benzyl-5H-dibenz[b,f]azepine, treating the resultant 5-benzyl-10,11-dihalogeno-10,11-dihydro-5H-dibenz[b,f]azepine with an inorganic or organic base, e.g. ethyl diisopropylamine or 1,5-diazabicyclo[4.3.0.]non-5-ene, to split off hydrogen halide, and finally splitting off the benzyl radical from the 5-benzyl-10-chloro- and 5-benzyl-10-bromo-5H-dibenz[b,f]azepine by heating each of these latter in conc. hydrochloric acid and hydrobromic acid respectively, if appropriate in admixture with glacial acetic acid.

Instead of 5-benzyl-5H-dibenz[b,f]azepine, it is also possible to use as starting material a 5-acyl-5H-dibenz[b,f]azepine with an easily removable 5-acyl group, for example 5-acetyl-5H-dibenz[b,f]azepine, or, for the manufacture of the 10-bromo compound, in particular 5-(trifluoroacetyl)-5H-dibenz[b,f]azepine, and to add chlorine or bromine to these compounds, then to split off hydrogen halide from the resultant 5-acyl-10,11-dihalogeno-5H-dibenz[b,f]azepines in the manner indicated hereinbefore, and finally to convert the respective 5-acyl-10-halogeno-5H-dibenz[b,f]azepine into 10-chloro- or 10-bromo-5H-dibenz[b,f]azepine by heating it with concentrated hydrobromic acid or, if a trifluoroacetyl radical is present, also by heating it with dilute, for example normal, sodium hydroxide solution.

10,11-Dihalogeno-5H-dibenz[b,f]azepines are manufactured by adding, for example, chlorine or bromine to the 5-acyl-10-halogeno-5H-dibenz[b,f]azepines previously mentioned and splitting off first hydrogen chloride and then the acyl radical from the 5-acyl-10,10,11-trihalogeno-10,11-dihydro-5H-dibenz[b,f]azepines, as indicated hereinbefore in respect of the corresponding 5-acyl-10,11-dihalogeno-10,11-dihydro-5H-dibenz[b,f-]azepines.

To split off hydrogen chloride from a compound of general formula III there is used, for example, a tertiary organic base, such as triethylamine, tributylamine, pyridine, collidine, or especially ethyl diisopropylamine or 1,5-diazabicyclo[4.3.0]non-5-ene, in the presence or absence of an organic solvent or diluent, for example dimethyl formamide, at elevated temperature, or also an inorganic base, for example sodium or potassium carbonate, in an organic solvent, for example dioxan or tetrahydrofuran, at elevated temperature, or potassium or sodium hydroxide in an organic solvent, for example in absolute ethanol or dioxan, at room temperature or slightly elevated temperature.

Starting materials of general formula III, in which $Y_2$ in conformity with "Hal" represents chlorine or bromine and R represents hydrogen, can be obtained in simple manner by addition of these halogens to 5H-dibenz[b,f]azepine-5-carboxamide in an inert organic solvent, for example a halogenated hydrocarbon, such as chloroform, preferably at or near room temperature. The starting material in which "Hal" is chlorine and $Y_2$ is iodine is obtained by addition of iodine chloride to 5H-dibenz[b,f]azepine-5-carboxamide, for example in dioxan. Starting materials of general formula III with a halogen atom R are obtained in analogous manner by using as starting material for the addition reactions mentioned above a 10-halogeno-5H-dibenz[b,f]azepine-5-carboxamide of general formula I instead of 5H-dibenz[b,f]azepine-5-carboxamide. Further starting materials of general formula III can be obtained by methods which are known per se.

As has been stated previously, the novel active substances can be administered perorally or rectally. The dosage depends on the mode of application, species, age and individual condition. For warm blooded animals the daily doses of active substances are from app. 0.5 mg/kg and 10 mg/kg. Suitable dosage unit forms, for example dragées, tablets or suppositories, contain preferably 20–200 mg of an active substance according to the invention.

Dosage unit forms for peroral administration contain as active substance preferably between 10–90% of a compound of formula I. These dosage forms are manufactured by combining the active substance e.g. with solid, pulverulent carriers, such as lactose, saccharose, sorbitol, mannitol; starches, such as potato starch, maize starch or amylopectin, also with laminaria powder or citrus pulp powder; cellulose derivatives or gelatins, if appropriate with the addition of lubricants, such as magnesium or calcium stearate or polyethylene glycols, to form tablets or dragée cores. The dragée cores are coated, for example, with concentrated sugar solutions which contain e.g. gum arabic, talcum and/or titanium dioxide, or with a lacquer which is dissolved in readily volatile organic solvents or solvent mixtures. Colourants can be added to these coatings, for example to distinguish different active substance concentrations.

Further suitable dosage unit forms are push-fit capsules made from gelatin as well as soft, sealed capsules of gelatin and a softener, such as glycerol. The push-fit capsules contain the active substance preferably in granule form, e.g. in admixture with fillers, such as maize starch, and/or lubricants, such as talcum or magnesium stearate, and, if appropriate, stabilisers, such as sodium metabisulphite ($Na_2S_2O_5$) or ascorbic acid. In soft capsules, the active substance is preferably dissolved or suspended in suitable liquids, for example liquid polyethylene glycols, to which it is also possible to add stabilisers.

Suitable dosage unit forms for rectal administration are, for example, suppositories, which consist of a combination of an active substance with a suppository base composition. As suppository base composition there are suitable, for example, natural or synthetic triglycerides, paraffin hydrocarbons, polyethylene glycols or higher alkanols. Also suitable are gelatin rectal capsules which consist of a combination of the active substance and a base composition. As base composition there are suitable, for example, liquid triglycerides, polyethylene glycols or paraffin hydrocarbons.

The following directions will serve to illustrate the manufacture of tablets, dragées, capsules and suppositories in more detail:

a. 500 g of 10-fluoro-5H-dibenz[b,f]azepine-5-carboxamide are mixed with 550 g of lactose and 292 g of potato starch and the mix is moistened with a solution of 8 g of gelatin in alcohol and granulated through a sieve. After the granules have been dried they are mixed with 60 g of potato starch, 60 g of talcum, 10 g of magnesium stearate and 20 g of highly disperse silica and the mix is pressed into 10,000 tablets each weighing 150 mg and containing 50 mg of active substance. If desired, the tablets can be provided with a breaking notch to adjust the dosage more finely.

b. A granulate is prepared from 1000 g of 10-chloro-5H-dibenz[b,f]azepine-5-carboxamide, 379 g of lactose and an aqueous solution of 6 g of gelatin. After it has been dried, the granulate is mixed with 10 g of colloidal silica, 40 g of talcum, 60 g of potato starch and 5 g of magnesium stearate and pressed into 10,000 dragée cores. These cores are then coated with a concentrated syrup of 533.5 g of crystalline saccharose, 20 g of shellack, 75 g of gum arabic, 250 g of talcum, 20 g of colloidal silica and 1.5 g of colourant. The resultant dragées each weigh 240 mg and contain 100 mg of active substance.

c. 1000 capsules each containing 75 mg of active substance are manufactured by mixing 75 g of 10-fluoro-5H-dibenz[b,f]azepine-5-carboxamide with 198 g of lactose, moistening the mix uniformly with an aqueous solution of 2 g of gelatin and granulating it through an appropriate sieve (e.g. sieve III according to Ph. Helv. V). The granulate is mixed with 10 g of dried maize starch and 15 g of talcum and packed uniformly into 1000 hard gelatin capsules of size I.

d. A suppository composition is prepared from 10 g of 10-chloro-5H-dibenz[b,f]azepine-5-carboxamide and 158.5 g of adeps solidus and cast into 100 suppositories each containing 100 mg of active substance.

The following Examples illustrate the manufacture of the novel compounds of formula I and of hitherto unknown starting materials, but do not in any way restrict the scope of the invention.

EXAMPLE 1

A mixture of 2.3 g of 10-fluoro-5H-dibenz[b,f]azepine and 30 ml of toluene saturated with phosgene is stirred for 2 days at 25° C. Excess phosgene is then expelled with nitrogen and the reaction mixture is concentrated by rotary evaporation to yield crude 10-fluoro-5H-dibenz[b,f]azepine-5-carbonyl chloride as residue.

This crude product is dissolved in 100 ml of dioxan, 50 ml of conc. ammonia solution are added and the solution is refluxed for 3 hours. It is then cooled to 25° C, the same volume of saturated sodium chloride solution is added and extraction is effected with ethyl acetate. The organic phase is separated, dried over magnesium sulphate and evaporated in vacuo. The residue is chromatographed through 50 times the amount of silica gel (particle size:0.063-0.2 mm) with ethyl acetate/methanol (7:1) as eluant. The homogeneous fractions are combined and concentrated by rotary evaporation. Crystallisation of the residue from ethyl acetate/petroleum ether yields 10-fluoro-5H-dibenz[b,f]azepine-5-carboxamide of m.p. 174°-177° C.

The starting material is manufactured as follows:

a. A mixture of 149.7 g (0.5 mole) of 5-benzyl-5,11-dihydro-10H-dibenz[b,f]azepin-10-one (vide British Pat. No. 961 444),27 ml of hydrogen fluoride, 125 g of sulphur tetrafluoride and 400 ml of methylene chloride is heated in a steel autocalve for 16 hours to 70° C. After the mixture has cooled, the bulk of the liquid constituents are filtered off with suction. Then water and aqueous ammonia solution are added until the pH of the aqueous phase is 9-10. The organic phase is separated, washed three times with water, diluted with 200 ml of benzene and concentrated in a rotary evaporator. The black residue is dissolved in methylene chloride and the solution is filtered through 700 g of silica gel (particle size 0.063-0.2 mm) with methylene chloride as eluant. The filtrate is concentrated, the residue dissolved in 1.5 liters of benzene and stirred for 30 minutes with 500 g of magnesium silicate gel. The mixture is filtered and 500 g of magnesium silicate gel are again added to the filtrate. After repeated filtration, the solution is concentrated in vacuo and the black residue is chromatographed over 800 g of silica gel (particle size 0.063-0.2 mm) with hexane/benzene (2:1) as eluant. The homogeneous fractions are combined and concentrated to yield the 5-benzyl-10-fluoro-5H-dibenz[b,f]azepine as a light yellow oil.

b. A solution of 6.03 g (0.02 mole) of 5-benzyl-10-fluoro-5H-dibenz[b,f]azepine in 100 ml of methanol is hydrogenated at 25° C in the presence of 0.6 of palladium on charcoal catalyst (5% Pd) until the uptake of hydrogen has ceased (app. 15 hours). The catalyst is filtered off and the filtrate is concentrated in vacuo. The residual colourless oil is chromatographed over 50 times the amount of silica gel (particle size: 0.063-0.2 mm) with benzene/petroleum ether (1:1) as eluant. The homogeneous fractions are combined, concentrated by rotary evaporation and the residue is crystallised from ether/hexane to yield 10-fluoro-5H-dibenz[b,f]azepine of m.p. 69°-72° C.

EXAMPLE 2

11.8 g (0.04 mole) of 10,11-dichloro-10,11-dihydro-5H-dibenz[b,f]azepine-5-carboxamide are suspended in 40 ml of pure dimethyl formamide. The suspension is cooled to 0°-10° C, whereupon it turns yellowish green in colour. With cooling and stirring, 11.8 ml of 1,5-diazabicyclo[4.3.0]non-5-ene are then added dropwise in the course of 10 minutes and stirring is continued for 30 minutes at 25° C and for 10 minutes at 60°-65° C. The mixture is then poured onto a mixture of 300 ml of water and ice, the resultant suspension is extracted with ethyl acetate and the aqueous phase is separated. The resultant ethyl acetate solution is washed with 200 ml of water, dried with calcium chloride, filtered with suction through activated charcoal/diatomaceous earth and the filtrate is concentrated by rotary evaporation. The residue is dissolved hot in 20 ml of acetonitrile, diluted with 12 ml of ether and cooled, when the 10-chloro-5H-dibenz[b,f]azepine-5-carboxamide crystallises out.

The starting material is manufactured as follows:

a. 11.8 g (0.05 mole) of 5H-dibenz[b,f]azepine-5-carboxamide are dissolved in 80 ml of chloroform at 25° C and chlorine gas is bubbled in, with stirring, at 15°-25° C until the precipitate which forms no longer increases (duration app. 4 to 5 hours). Then the resultant 10,11-dichloro-10,11-dihydro-5H-dibenz[b,f]azepine-5-carboxamide is filtered off with suction and washed with a small amount of chloroform. The product is dried cautiously at 70° C in a high vacuum, whereupon it melts with decomposition at 140°-142° C.

EXAMPLE 3

With cooling at 5°-10° C, 12 g (app. 0.03 mole) of the crude 10,11-dibromo-10,11-dihydro-5H-dibenz[b,f]azepine-5-carboxamide obtained according to (a) are suspended in 35 ml of dimethyl formamide. With stirring, 10 g (app. 0.08 mole) of 1,5-diazabicyclo[4.3.0]non-5-ene are added dropwise at 5°-10° C. Stirring is continued for 2 hours at 25° C and a new precipitate forms. The reaction mixture is then heated for 10 minutes to 90°-100° C and, after it has cooled, poured onto a mixture of water and ice and the organic phase is dissolved in ethyl acetate. The aqueous phase is then separated and the organic phase is washed with water, dried over calcium chloride and evaporated in a water jet vacuum. The residue is crystallised from 30 ml of acetonitrile to yield light green 10-bromo-5-H-dibenz[b,f]azepine-5-carboxamide of m.p. 168°-170° C.

The starting material is manufactured as follows:

a. 11.8 g (0.05 mole) of 5H-dibenz[b,f]azepine-5-carboxamide are dissolved at app. 25° C in 80 ml of chloroform. With gentle cooling, 8.2 g of bromine (0.1025 mole) in 40 ml of chloroform are added dropwise with stirring at 15°-25° C in the course of 40 minutes. After about one third of this amount has been added, a precipitate forms which becomes more dense as the dropwise addition continues. The batch is subsequently stirred for a further 2 hours and the reaction product is then filtered off with suction. The filter cake is washed with a small amount of chloroform and then dried for 8 hours in a high vacuum at 70°-80° C to yield the crude 10,11-dibromo-10,11-dihydro-5H-dibenz[b,f]azepine-5-carboxamide which melts at 144.5° C with decomposition.

EXAMPLE 4

In analogous manner to Example 1, 10-chloro-5H-dibenz[b,f]azepine-5-carboxamide which melts at 183°-185° C is obtained by starting from 2.51 g (0.011 mole) of 10-chloro-5H-dibenz[b,f]azepine.

The starting material is manufactured as follows:

a. 7.7 g (0.11 mole) of chlorine are bubbled into 240 ml of chloroform at 0°-5° C. Then a solution of 23.7 g (0.1 mole) of 5-acetyl-5H-dibenz[b,f]azepine in 50 ml of chloforum are added dropwise in the course of 30 minutes with the temperature still being held between 0° and 5° C. Upon completion of the dropwise addition, the reaction mixture is stirred for a further 16 hours at 5°-10° C and the solvent is subsequently evaporated off completely by rotary evaporation and the residue, 5-acetyl-10,11-dichloro-10,11-dihydro-dibenz[b,f]azepine, crystallises out after addition of ether in the form of a cis/trans-isomer mixture; m.p. 137°-152° C.

b. With stirring, 10.7 g (0.035 mole) of the isomer mixture of 5-acetyl-10,11-dichloro-10,11-dihydro-5H-dibenz[b,f]azepine, 21 ml of dimethyl formamide and 11 ml of diisopropyl ethylamine are heated for 3 hours to 120° C. The reaction mixture is then stirred into 500 ml of water and the precipitated oil is extracted with ether. The organic phase is separated, washed with 2 normal hydrochloric acid and then with water, dried over sodium sulphate and then concentrated, whereupon 5-acetyl-10-chloro-5H-dibenz[b,f]azepine crystallises out; m.p. 85°-88° C.

c. With stirring, 9 g (0.033 mole) of 5-acetyl-10-chloro-5H-dibenz[b,f]azepine, 30 ml of toluene and 18 ml of 48% hydrobromic acid are heated to 90° C for 5 hours. The reaction mixture is then allowed to cool to room temperature and the precipitated 10-chloro-5H-dibenz[b,f]azepine hydrobromide is filtered off with suction. The crude hydrobromide is treated at room temperature with 10% aqueous ammonia solution and the precipitated 10-chloro-5H-dibenz[b,f]azepine is taken up in ether. The ethereal solution is washed with water, dried over potassium carbonate and concentrated by evaporation. The substance melts at 78°-80° C.

EXAMPLE 5

10-Bromo-5H-dibenz[b,f]azepine-5-carboxamide (m.p. 168°-170° C) is obtained in analogous manner to Example 1 by starting from 3 g (0.011 mole) of 10-bromo-5H-dibenz[b,f]azepine.

The starting material is manufactured as follows:

a. With stirring and cooling with ice, 79.17 ml (0.569 mole) of trifluoroacetic acid anhydride are added dropwise to a solution of 100 g (0.517 mole) of 5H-dibenz[b,f]azepine in 1000 ml of benzene in such a manner that the temperature does not exceed 30° C. After a further 4 hours, 79.5 ml of triethylamine are added to neutralise the trifluoroacetic acid that has formed and the reaction mixture is then shaken out with 500 ml of water. The organic phase is separated, washed with saturated sodium chloride solution, dried over sodium sulphate and concentrated by rotary evaporation until the first crystals form. After addition of petroleum ether, 5-(trifluoroacetyl)-5H-dibenz[b,f]azepine is obtained as crystals with a melting point of 86°-99° C. The crystallisation of the mother liquor yields still further substance which melts at 85°-91° C, cf. Edward Gipstein et al., Anal. Calorimetry. Proc. Symp. second, 1970, 127-34 (C.A. 74, 125016n).

b. With stirring, 74.2 g (0.465 mole) of bromine are added dropwise to a solution of 128.06 g of 5-(trifluoroacetyl)-5H-dibenz[b,f]azepine (0.443 mole) in 1000 ml of chloroform. After 3 hours, 1000 ml of petroleum ether are added to the resultant suspension and the crystals which have formed are filtered off and dried for 16 hours at 25° C/60 Torr to yield 10,11-dibromo-10,11-dihydro-5-(trifluoroacetyl)-5H-dibenz[b,f]azepine which melts at 186°-189° C.

c. A solution of 138.1 g of 10,11-dibromo-10,11-dihydro-5-(trifluoroacetyl)-5H-dibenz[b,f]azepine in 580 ml of dimethyl formamide is treated at 0°-10° C with 114.5 ml of 1,5-diazabicyclo[5.4.0]undec-5-ene and stirred for 1 hour at the same temperature. The dark solution is then poured into a mixture of water and ice and the resultant suspension is extracted with ethyl acetate. The organic phase is washed with saturated sodium chloride solution, dried over magnesium sulphate and concentrated by evaporation, to yield crude, syrupy 10-bromo-5-(trifluoroacetyl)-5H-dibenz[b,f]azepine which is directly processed further.

d. A solution of 85.9 g of 10-bromo-5-(trifluoroacetyl)-5H-dibenz[b,f]azepine in 500 ml of methanol and 233 ml of normal sodium hydroxide solution is refluxed for 2 hours. The methanol is evaporated off, the concentrated reaction mixture diluted with water and extracted with ethyl acetate. The organic phase is washed with saturated sodium chloride solution, dried over magnesium sulphate and concentrated by evaporation. The residue is purified by chromatography over 380 g of silica gel with benzene/petroleum ether (1:1) as eluant. The fraction containing pure 10-bromo-5H-dibenz[b,f]azepine are combined and concentrated by evaporation. The residue is crystallised from cyclohexane to yield 10-bromo-5H-dibenz[b,f]azepine which melts at 65°-69° C.

EXAMPLE 6

A solution of 8.33 g of crude 10,11-dihydro-10,10,11-trichloro-5H-dibenz[b,f]azepine-5-carboxamide in 35 ml of dimethyl formamide is treated at 0°-10° C with 9.1 ml (0.61 mole) of 1,5-diazabicyclo[5.4.0]undec-5-ene and stirred for 1 hour at room temperature. The brown solution is then poured into a mixture of water and ice and the resultant suspension is extracted with ethyl acetate. The organic phase is washed with saturated sodium chloride solution, dried over magnesium sulphate and concentrated by evaporation. The crude product is chromatographed over silica gel (particle size: 0.063-0.2 mm) with ethyl acetate as eluant. The homogeneous fractions are combined, concentrated by evaporation and recrystallised from ethyl acetate to yield 10,11-dichloro-5H-dibenz[b,f]azepine-5-carboxamide which melts at 265°-270° C.

10-Chloro-11-fluoro-5H-dibenz[b,f]azepine-5-carboxamide is obtained in analogous manner by using 7.9 g of crude 10,11-dichloro-10,11-dihydro-10-fluoro-5H-dibenz[b,f]azepine-5-carboxamide.

The starting materials are manufactured as follows:

a. 6.8 g (0.025 mole) of 10-chloro-5H-dibenz[b,f]azepine-5-carboxamide are dissolved in 45 ml of chloroform and chlorine is bubbled into the solution at 15°-25° C over the course of 2 hours. The resultant suspension is stirred for a further 1½ hours and blown out with nitrogen for 1 hour. The reaction mixture is cooled, diluted with a small amount of petroleum ether and filtered. Crude 10,11-dihydro-10,10,11-trichloro-5H-dibenz[b,f]azepine-5-carboxamide which can be processed further without purification is obtained as filter product.

Crude 10,11-dichloro-10,11-dihydro-10-fluoro-5H-dibenz[b,f]azepine-5-carboxamide is obtained in analogous manner by starting from 6.35 g (0.025 mole) of 10-fluoro-5H-dibenz[b,f]azepine-5-carboxamide.

EXAMPLE 7

In analogous manner to Example 3, 10-bromo-11-chloro-5H-dibenz[b,f]azepine-5-carboxamide is obtained by starting from 13 g (app. 0.03 mole) of crude 10-chloro-10,11-dibromo-5H-dibenz[b,f]azepine-5-carboxamide (vide a).

a. The starting material is obtained in analogous manner to Example 3 a) by using 13.55 g (0.05 mole) of 10-chloro-5H-dibenz[b,f]azepine-5-carboxamide.

What we claim is:

1. A compound 5H-dibenz[b,f]azepine of formula I

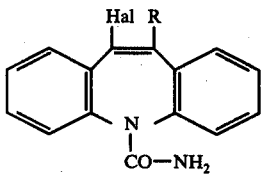

wherein Hal represents halogen with an atomic number up to 35 and R represents hydrogen or halogen with an atomic number up to 35.

2. A compound according to claim 1 having the formula I given in claim 1, wherein R represents hydrogen and Hal has the meaning given in claim 1.

3. A compound according to claim 1 having the formula I given in claim 1, wherein Hal and R represent halogen atoms with an atomic number up to 35.

4. A compound according to claim 1 which is 10-fluoro-5H-dibenz[b,f]azepine-5-carboxamide.

5. A compound according to claim 1 which is 10-chloro-5H-dibenz[b,f]azepine-5-carboxamide.

6. A compound according to claim 1 which is 10-bromo-5H-dibenz[b,f]azepine-5-carboxamide.

7. A compound according to claim 1 which is 10,11-dichloro-5H-dibenz[b,f]azepine-5-carboxamide.

8. A pharmaceutical composition useful in the treatment of states of convulsion comprising an anticonvulsively effective amount of a compound according to claim 1 and having the formula I

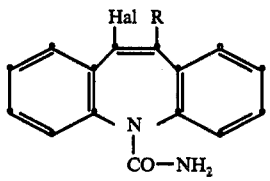

wherein Hal represents halogen with an atomic number up to 35 and R represents hydrogen or halogen with an atomic number up to 35 together with pulverulent carriers or a suppository base composition.

9. A pharmaceutical composition according to claim 8 wherein an anticonvulsively effective amount of a compound of formula I, wherein Hal represents halogen with an atomic number up to 35 and R represents hydrogen, is present.

10. A pharmaceutical composition according to claim 8 wherein an anticonvulsively effective amount of a compound of formula I, wherein Hal and R each represent halogen with an atomic number up to 35, is present.

11. A pharmaceutical composition according to claim 8 wherein an anticonvulsively effective amount of 10-fluoro-5H-dibenz[b,f]azepine-5-carboxamide is present.

12. A pharmaceutical composition according to claim 8 wherein an anticonvulsively effective amount of 10-chloro-5H-dibenz[b,f]azepine-5-carboxamide is present.

13. A pharmaceutical composition according to claim 8 wherein an anticonvulsively effective amount of 10-bromo-5H-dibenz[b,f]azepine-5-carboxamide is present.

14. A pharmaceutical composition according to claim 8 wherein an anticonvulsively effective amount of 10,11-dichloro-5H-dibenz[b,f]azepine-5-carboxamide is present.

15. A method for the treatment of a state of convulsion in a warm-blooded animal comprising administration to said animal of a therapeutically effective amount of a compound according to claim 1 having the formula I

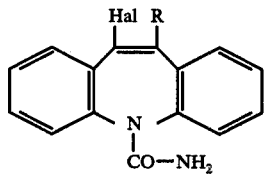

wherein Hal represents halogen with an atomic number up to 35 and R represents hydrogen or halogen with an atomic number up to 35.

* * * * *